(12) United States Patent
Von Mandach

(10) Patent No.: US 10,405,948 B2
(45) Date of Patent: Sep. 10, 2019

(54) ORTHODONTIC APPLIANCE

(71) Applicant: Christoph Von Mandach, Bözberg (CH)

(72) Inventor: Christoph Von Mandach, Bözberg (CH)

( * ) Notice: Subject to any disclaimer, the term of this patent is extended or adjusted under 35 U.S.C. 154(b) by 0 days.

(21) Appl. No.: 15/522,753

(22) PCT Filed: Oct. 22, 2015

(86) PCT No.: PCT/EP2015/074448
§ 371 (c)(1),
(2) Date: Apr. 27, 2017

(87) PCT Pub. No.: WO2016/066514
PCT Pub. Date: May 6, 2016

(65) Prior Publication Data
US 2017/0333162 A1 Nov. 23, 2017

(30) Foreign Application Priority Data

Oct. 29, 2014 (CH) ..................................... 1664/14

(51) Int. Cl.
*A61C 7/14* (2006.01)
*A61C 7/02* (2006.01)
(Continued)

(52) U.S. Cl.
CPC ................ *A61C 7/146* (2013.01); *A61C 7/02* (2013.01); *A61C 7/143* (2013.01); *A61C 7/148* (2013.01);
(Continued)

(58) Field of Classification Search
CPC ......... A61C 7/146; A61C 7/148; A61C 7/282; A61C 7/026; A61C 7/303; A61C 7/16;
(Continued)

(56) References Cited

U.S. PATENT DOCUMENTS

| 678,453 A | 7/1901 | Angle |
|---|---|---|
| 1,204,114 A | 11/1916 | Angle |

(Continued)

FOREIGN PATENT DOCUMENTS

| WO | 2005/107629 | 11/2005 |
|---|---|---|
| WO | 2015/140026 A1 | 9/2015 |

OTHER PUBLICATIONS

International Preliminary Report on Patentability, dated May 2, 2017, International App No. PCT/EP2015/074448.

*Primary Examiner* — Heidi M Eide
(74) *Attorney, Agent, or Firm* — DWC Law Firm, P.S.; Ann W. Speckman; David Chen

(57) ABSTRACT

The invention relates to an orthodontic device which is particularly economical and as small as possible, and which has hooks and a small tube, produced from a sheet metal plate using stamping and bending techniques and without the use of welding or soldering. The orthodontic device comprises a base plate having a flat region with a gingival and an occlusal edge. An occlusal rolling forms the small tube. The gingival edge has a counter-directional rolling. Concave cuts are formed in the side edges in order to form wing-shaped hooks. Both rollings can hold an applicator/protector, with which the orthodontic device is protected during adhesion, and can then be applied to a tooth in the correct orientation.

14 Claims, 7 Drawing Sheets

(51) Int. Cl.
*A61C 7/30* (2006.01)
*A61C 7/28* (2006.01)

(52) U.S. Cl.
CPC ............... *A61C 7/282* (2013.01); *A61C 7/30* (2013.01); *A61C 7/026* (2013.01); *A61C 7/303* (2013.01)

(58) Field of Classification Search
CPC .... A61C 7/14; A61C 7/12; A61C 7/02; A61C 7/143; A61C 7/30
See application file for complete search history.

(56) References Cited

U.S. PATENT DOCUMENTS

| | | |
|---|---|---|
| 3,052,028 A | 9/1962 | Wallshein |
| 3,075,287 A | 1/1963 | Weinger |
| 3,639,986 A | 2/1972 | Kesling |
| 4,028,809 A | 6/1977 | Wallshein |
| 4,626,208 A | 12/1986 | Hall |
| 4,781,582 A | 11/1988 | Kesling |
| 5,320,526 A | 6/1994 | Tuneberg |
| 5,474,444 A * | 12/1995 | Wildman ................. A61C 7/12 433/18 |
| 5,542,842 A | 8/1996 | Andreiko |
| 6,241,516 B1 * | 6/2001 | Orikasa ................. A61C 7/282 433/17 |
| 8,235,714 B2 | 8/2012 | Hagelganz et al. |
| 8,444,414 B2 | 5/2013 | Moon et al. |
| 2005/0227196 A1 | 10/2005 | Von Mandach |

* cited by examiner

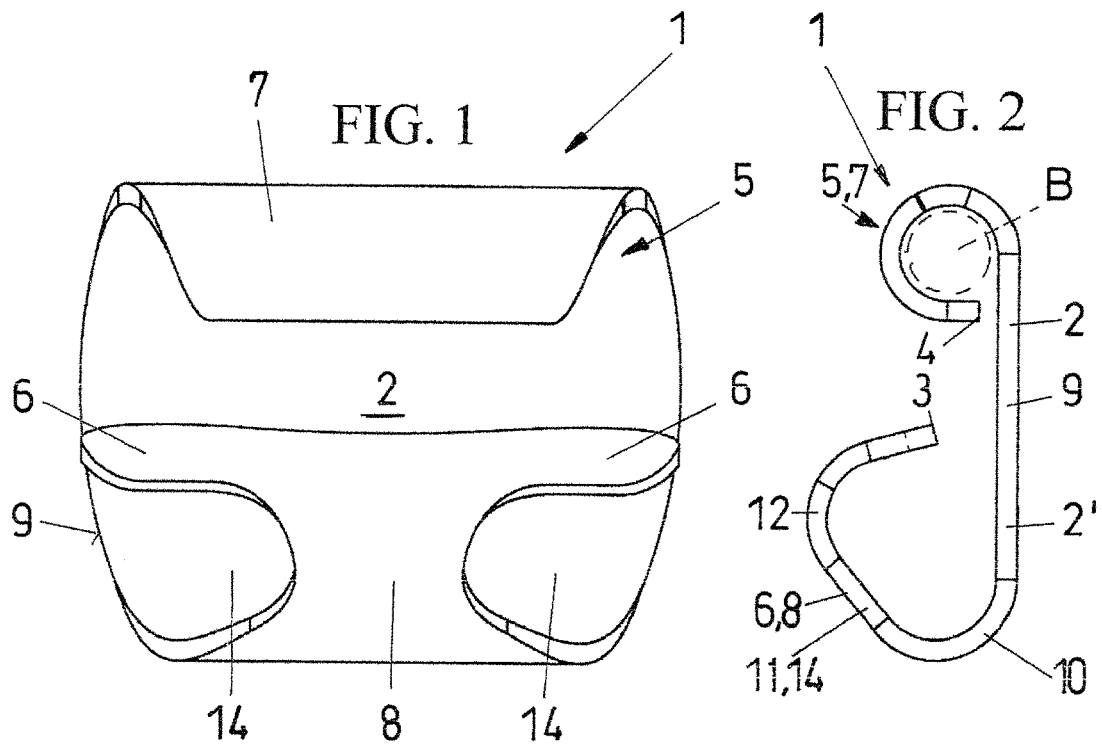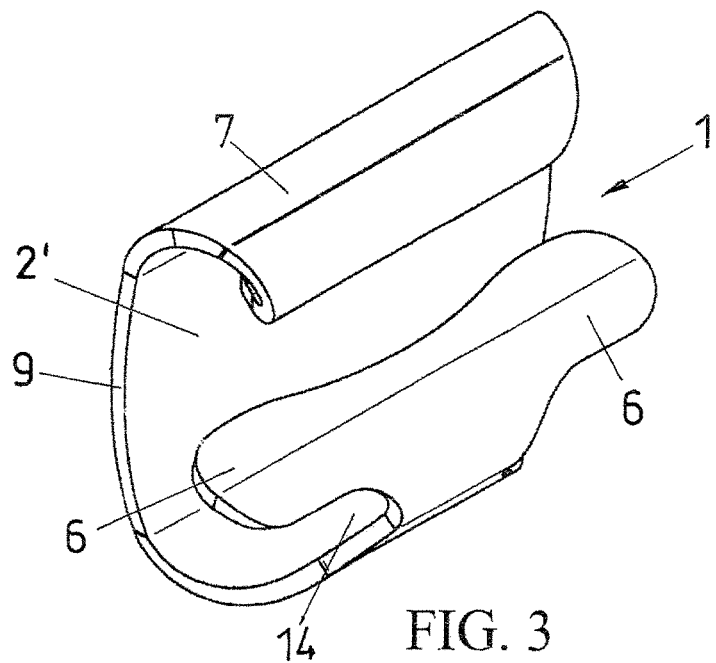

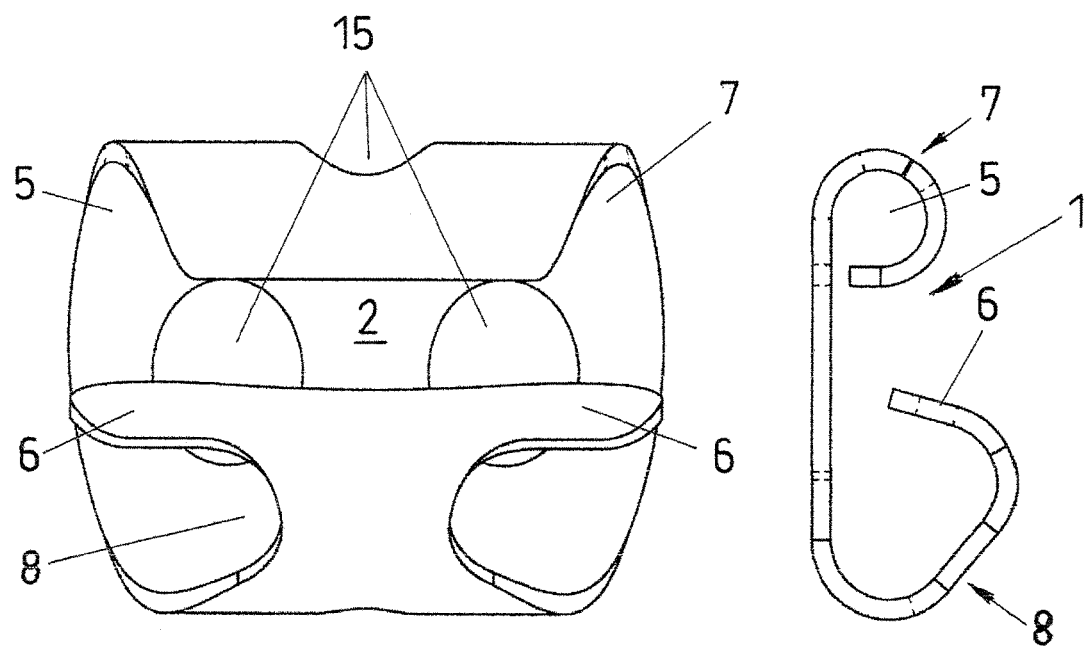
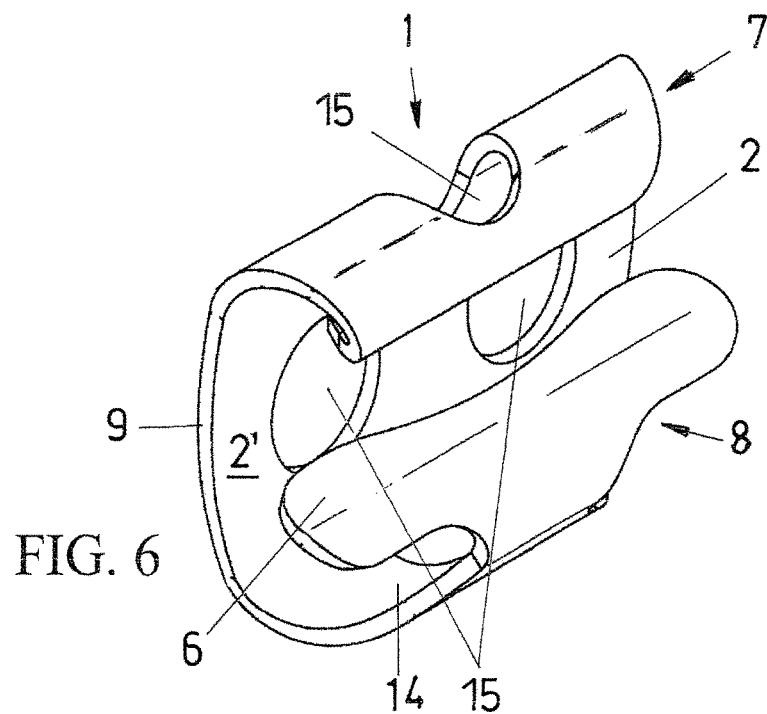

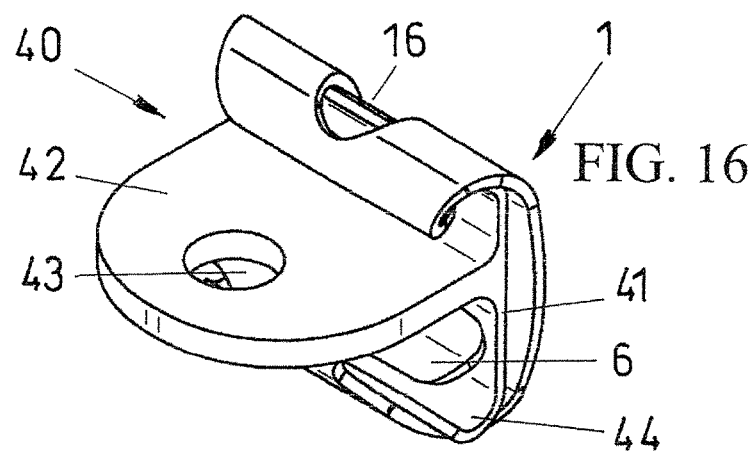
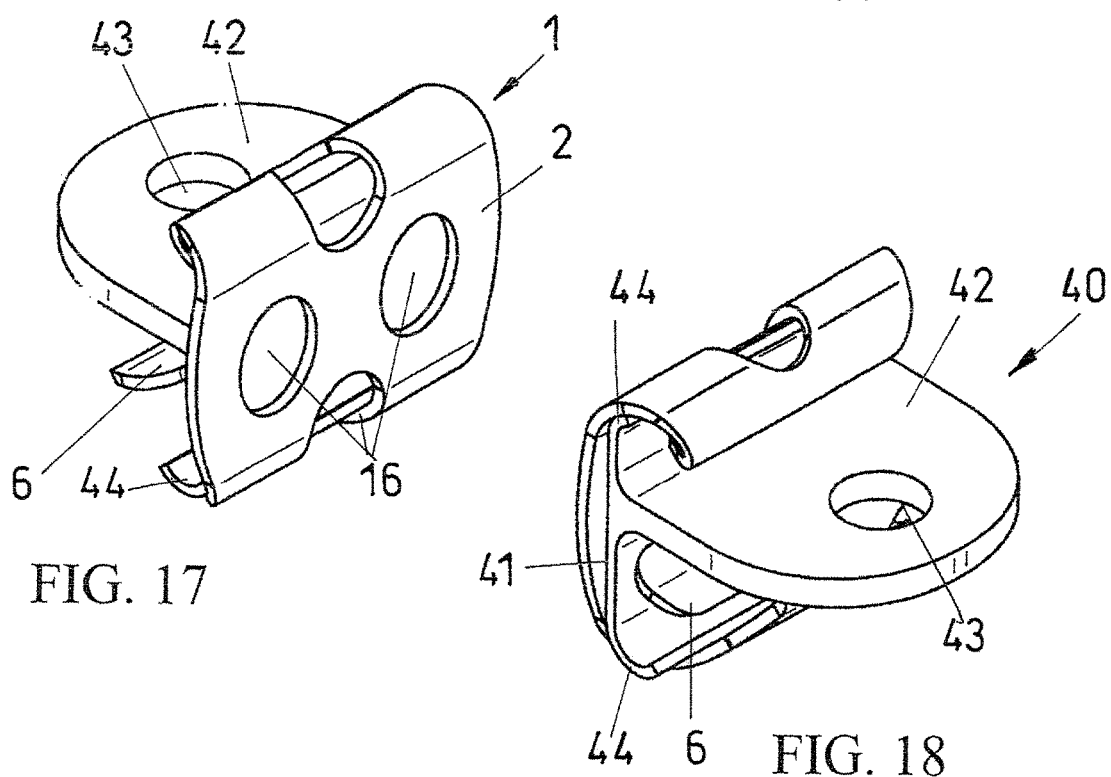

ORTHODONTIC APPLIANCE

REFERENCE TO RELATED APPLICATIONS

This application is the US national phase entry of International Patent Application no. PCT/EP2015/074448, filed Oct. 22, 2015, which claims priority to Swiss patent application no. 1664/14, filed Oct. 29, 2014.

TECHNICAL FIELD

The present invention relates to an orthodontic appliance with hooks and with a tube for guiding and holding an archwire, comprising a base plate with at least one approximately plane region with an bonding side directed to the tooth and with an integrally formed hook for fastening rubber bands, ligatures and/or pull chains, wherein the appliance is manufactured from a sheet metal plate by way of stamping-bending technology, in a weld-free and solder-free manner.

BACKGROUND

Today's current treatment means for the correction of misalignments of teeth can be divided into removable and stationary appliances. Generally, stationary appliances are to be understood as brackets and tubes. They account for the majority of orthodontic appliances. Orthodontic appliances such as brackets and tubes are firstly aligned in a precise manner on the surface of the teeth and then firmly bonded. The edgewise brackets which have been known since 1925, apart from a slot, in which the orthodontic wire is led, comprise upwardly and downwardly directed bracket wings, via which the rubber O-rings or rubber chains or also elastic modules are pulled. These serve for holding the orthodontic wire which is to say the archwire, in the slot. Orthodontic appliances in the form of a tube also have a similar function. These tubes can be applied bucccally as well as lingually, but are mostly used as buccal tubes. Stationary orthodontic appliances such as bracket and tubes moreover also comprise hooks which serve as fastening parts for rubber bands, ligatures and/or pull chains.

STATE OF THE ART

Orthodontic appliances in the form of tubes belong to the oldest of orthodontic appliances. Edward H. Angle had already used such tubes, wherein these serve for the end-anchoring of the archwire and were soldered on so-called molar bands. As is evident from the corresponding patent U.S. Pat. No. 678,453, such tubes still had no hooks, since rubber bands were still not yet used at the time. Each individual tooth was pulled towards the archwire by way of ligatures. Edward Angle also used hooks as a separate element, and these in turn were fastened on a molar band. This is shown in U.S. Pat. No. 1,204,114. The U.S. Pat. No. 3,639,986 discloses a further tube. Here, the tube is manufactured as bar material and a section of this is welded or soldered on a flange which in turn was attached to a molar band. Here, the flange itself comprises a hook.

In a similar manner and according to U.S. Pat. No. 3,075,287, a molar band was designed having a web which crosses gingival-occlusally and below which a tube was pushed through. This solution however also does not disclose hooks.

Later, one departed from the approach of using tubes and hooks manufactured of sheet metal due to the design being very restricted on account of their manufacturing techniques. Such elements, just as the brackets of metal, have been increasingly manufactured in a material-removing manner since the occurrence of micro-technology, or have later been manufactured with the up-and-coming MIM (micromould injection) technology. This permitted almost every design shape as the following documents bear witness to, purely by way of example: U.S. Pat. Nos. 5,320,526; 4,781,582; WO 2005107629 or also the document U.S. Pat. No. 8,444,414. The solution according to U.S. Pat. No. 8,235,714 is somewhat special. What is suggested here is a bracket with a cover which can be attached to this in a clamping manner such that to bracket with the cover can be used as a tube, or without the cover as a conventional bracket.

A tube of the initial mentioned type is known from U.S. Pat. No. 4,028,809. Here, a tube with a hook and manufactured as one piece from sheet metal is evident. This tube is bent in a u-shaped manner from a sheet metal pate, and flanges which are suitable for fastening on a molar band are integrally formed on the vertical walls of this u-shaped part. However, the tube here merely consists of the u-shaped tunnel and the archwire runs in this tunnel. This tunnel runs parallel or in an inclined manner to the running direction of the lateral flanges, depending on the wishes and demands of the treating person. This results in the height as well as the width of this tunnel being significantly larger than the diameter of the archwire. However, the larger an orthodontic appliance, the greater are the irritations arising for the patient. The overall rectangular design moreover leads to sharp edges leading to injuries to the mucous membranes in the oral cavity. Nowadays, one wishes for the archwire to mostly be led along as closely as possible to the tooth surface. Such a demand could be met by the known tube, but since the tube in this case is not a tube, but merely a u-shaped tunnel, the archwire here bears directly on the tooth. This however can lead to damage to the tooth surface.

Significantly more complex design shapes which overcome the above-mentioned disadvantages can be realised thanks to the micro-technical bending-stamping methods which are possible today.

SUMMARY

Consequently, it is an object of the present invention, to provide a tube with a hook, of the initially mentioned type, with which no irritations occur at the patient, no damage to the dental surface can occur due to the archwire and the archwire can be guided in a tube in an exact manner.

This object is achieved by an orthodontic appliance with the features of patent claim 1.

A further object of the invention is to provide a means which simplifies the application of cement onto the orthodontic appliance and which protects the parts which are to remain free of cement, and as an applicator simplifies the positioning and attachment of the orthodontic appliance onto the desired tooth.

BRIEF DESCRIPTION OF THE DRAWINGS

Various embodiments of the subject-matter of the invention are represented in the accompanying drawing and are described by way of the subsequent description.

There are shown in:

FIGS. 1-3: a first embodiment of the orthodontic appliance according to the invention, in three views, specifically in a view from the top, in a lateral view and in a perspective representation.

FIG. 4-6 show a second embodiment which with regard to the shape corresponds to the first embodiment, but comprises relative large light passage openings, again in the same three representation manners as the first embodiment example

FIGS. 16-18 show the orthodontic appliance in the second embodiment according to FIGS. 4 to 6, with an inserted holding plate having an eyelet, wherein all three figures show perspective views from different viewing angles.

DESCRIPTION OF THE INVENTION

Three embodiment examples of the subject-matter of the invention are represented in FIGS. 1-9. Each embodiment is represented in each case in a plan view, a lateral view and a perspective representation. The orthodontic appliance as a whole is indicted at 1. The term orthodontic appliance has been selected here, in order to express its ability to be applied in a comprehensive manner Orthodontic appliances which consist only of hooks or only of tubes are known on the market. The solution of an orthodontic appliance which is specified here serves for both previously mentioned embodiments and can also assume bracket functions in an auxiliary manner. The term tube is also applied in a generalised manner, although such an appliance on the market is mostly called a buccal tube. Not only can such a tube be applied bucccally, but also lingually thanks to the small dimensions of the appliance according to the invention. The term lingual tube however is not commonly used.

Figure 19:
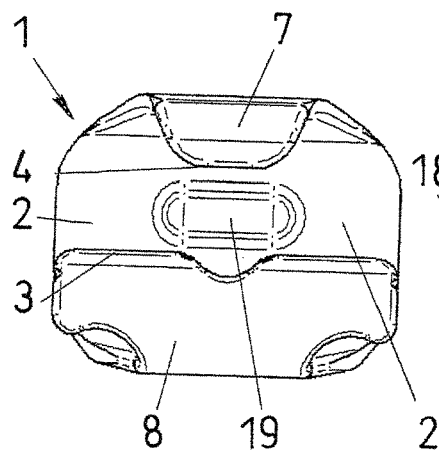
FIGS. 19-21 show an orthodontic appliance according to FIGS. 1-3, in an alternative embodiment, in a plan view, lateral view and in a perspective representation.
Figure 20:
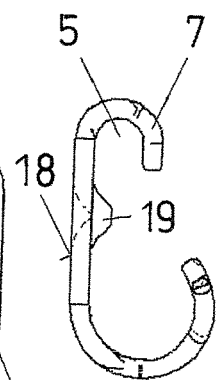
Figure 21:
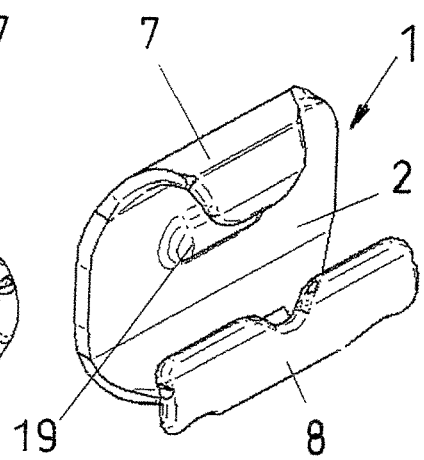
Figure 22:
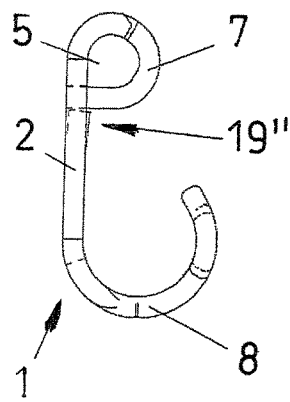
FIGS. 22-25 represent a further variant of the orthodontic appliance, again in a lateral view, a plan view and in two different perspective representations.
Figure 23:
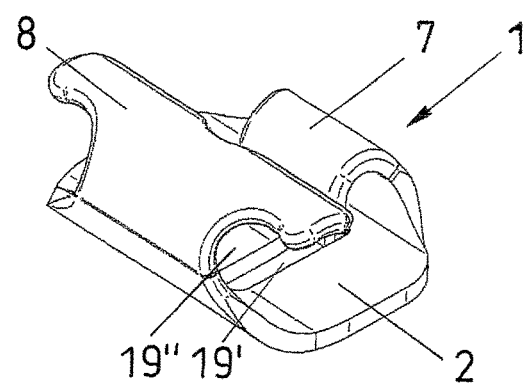
Figure 24:
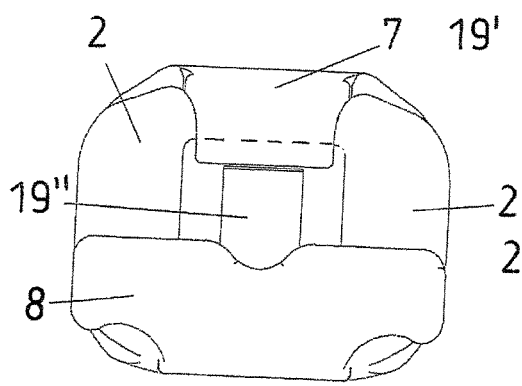
Figure 25:
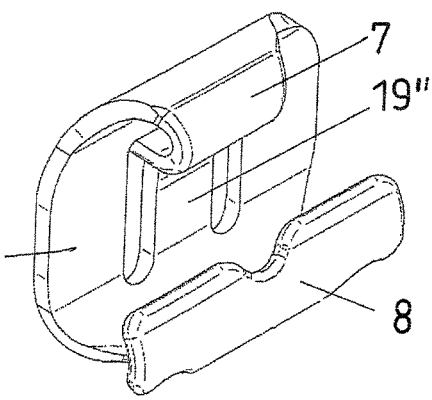

FIGS. 19-21 show an orthodontic appliance according to FIGS. 1-3, in an alternative embodiment, in a plan view, lateral view and in a perspective representation.

FIGS. 22-25 represent a further variant of the orthodontic appliance, again in a lateral view, a plan view and in two different perspective representations.

The orthodontic appliance 1 according to the invention is shaped in a weld-free and solder-free manner by way of bending-stamping methods. The thickness of such a sheet metal is selected between 0.1 mm and 0.5 mm. Preferably one would select the thinner sheet metals in the region of 0.1 mm to 0.3 mm Cold-rolled, soft cobalt-chromium-nickel sheet metals which can be worked or processed quite easily and subsequently hardened and tempered to a very high hardness are suitable for the orthodontic appliances of interest here. Such sheet metals of cobalt-chromium-nickel alloys are known on the market under the description Phynox, and are marketed for example by the company Matthey SA. Starting from a flat sheet metal, the orthodontic appliances which are of interest here can be manufactured at a very high cycle speed by way of stamping-bending tools All peripheral edges as well as possible openings can be shaped into the plane initial blank in a single stamping procedure and subsequently shaped from the two-dimensional form into the three-dimensional form by way of bending.

Here, the plane rolling of the metal stamping which is to say stamped part, before the bending is indicated as the base plate. The region of the base plate 1 which is not deformed by bending technology is indicated as the plane region Z. This region can be recognised particularly well in FIG. 2. This plane region 2' seems to be arched in FIGS. 1 and 3, but this is deceptive since the side edges 9 run arcuately within the plane in a convex manner. As already mentioned, the base plate 2 is delimited laterally by the side edges 9, whereas the upper edge is indicted as the occlusal edge 4 and the lower edge as the gingival edge 3. The occlusal edge is bent over by at least 200°, preferably however by 270°, towards the centre of the base plate 2. An occlusal rolling-in (curl) 7 which then forms the actual tube 5 thus arises. This tube is dimensioned such that an archwire B can be accommodated therein. In the embodiment represented here, this occlusal edge 4 is bent over towards the centre by about 270°, as can be recognised in FIG. 2.

Departing from the plane region 2' of the base plate 2, the gingival edge 3 is likewise bent towards the centre and away from the bonding side 17. Of course, the term "below the bonding side" is indicated as that surface of the base plate 2 which is directed to the surface of the tooth during use. This bending-over forms the gingival rolling-in 8. This gingival rolling-in 8 comprises a first bend 10 which connects to the plane region 2'. A section 11 running in a straight line follows this first bend 10. The first bend 10 covers less than 180°, preferably 120°-150°, so that a straight section 11 running obliquely upwards is formed. The second bend 12 which covers more than 90°, then follows this section 11 running in a straight manner This second bend preferably covers 100°-120°. An end section 13 running in a straight manner is subsequent to the second bend 12. Concave indentations 14 are present in both side edges 9. These concave indentations 14 come to lie in the region of the straight section 11 of the gingival rolling-in 8, in the completed bent condition of the orthodontic appliance 1. The hooks 6 are then formed by these concave indentations 14. The term hook is merely to be understood in that these serve for attaching rubber bands, ligatures and/or pull chains, but also O-rings. Here, these hooks have a wing-like design. These hooks or wings then for example engage through the eyelets of those rubber pull chains or O-rings, which are indicated as rubber bands. Wire connections which is to say so-called ligatures, can also be connected here.

FIGS. 4-6 show a second embodiment of the orthodontic appliance according to the invention. The outer contour corresponds completely to that of the first embodiment. Differing from the first embodiment, one can recognise several relatively large stamped-out light passage openings 15. Two of these light passage openings 15 are arranged next to one another and lie completely in the plane region 2'. Two further stamped-out light passage openings 15 lie partly in the occlusal rolling-in 7 and in the gingival rolling-in 8. The purpose of these light passage openings 15 lies in fastening such orthodontic appliances on the tooth by way of adhesives (cements) which are cured by light. If one were not to provide these light passage openings 15, then one would have to introduce the light laterally from the bracket between the surface of the tooth and the base pate 2, as is mostly effected nowadays. An improved passage of light thus leads to a quicker and more homogeneous curing of the cement. The proportion of detaching orthodontic appliances which even until now is relatively high would definitely be reduced by way of this.

Figure 7:
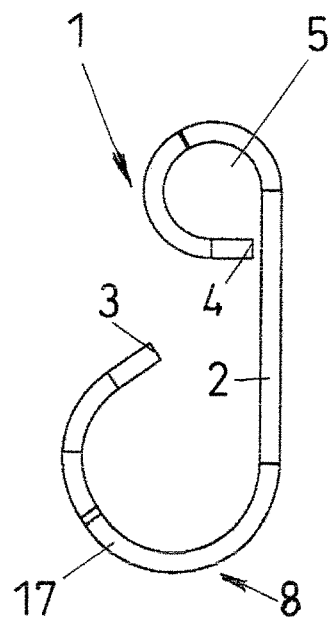
FIGS. 7-9 represent a third embodiment, with which the gingival edge is bent slightly differently and a multitude of small light passage openings is provided instead of a few large ones.
Figure 8:
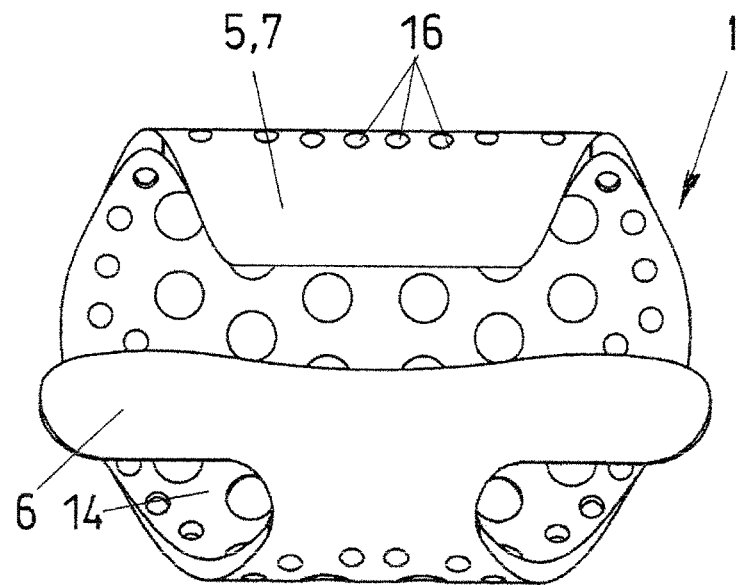
Figure 9:
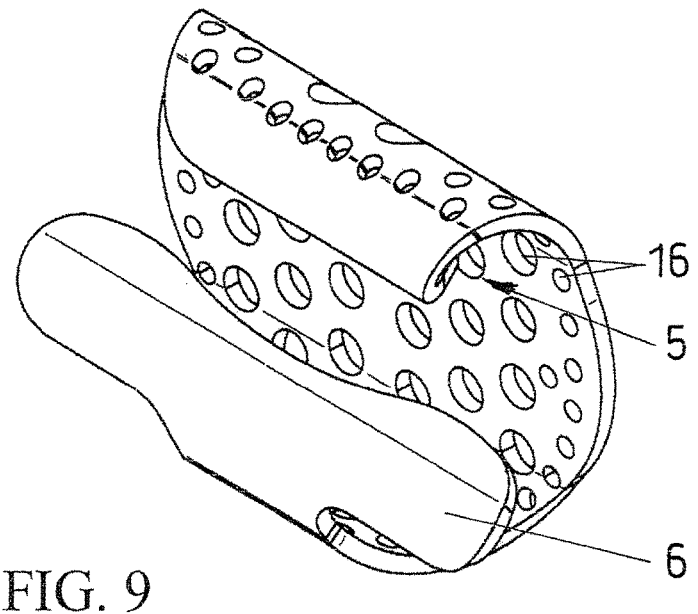
Figure 10:
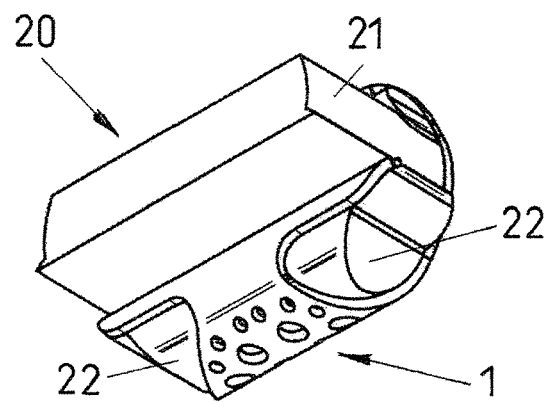
FIGS. 10-12 show an orthodontic appliance in the embodiment according to FIGS. 7-9, with an applicator which is simultaneously a protector, which is incorporated therein. These views are once perspectively with a view obliquely from below onto the gingival side, once in a lateral view and once again perspectively obliquely from above with a view onto the occlusal side of the orthodontic appliance.
Figure 11:
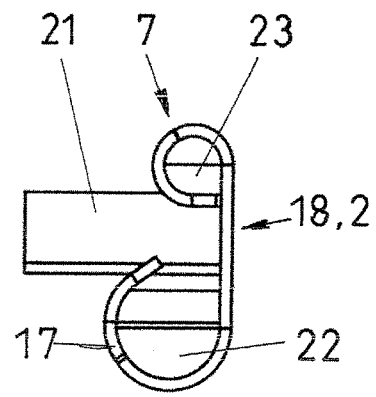
Figure 12:
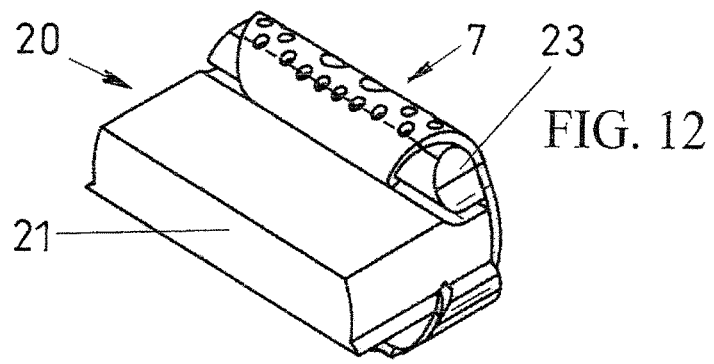

A third embodiment of the orthodontic appliance 1 is shown in FIGS. 7-9. The general design with regard to the shaping is essentially the same as the previously described embodiments. What is evident however is the fact that here the gingival rolling-in 8 for forming the wing-like hooks is shaped from a single bend 17. The distance between the gingival edge 3 and the plane region 2' of the base late 2 is enlarged somewhat by way of this, and this simplifies the design and introduction of an applicator.

Here, a multitude of small light passage openings 16 can be shaped in, instead of the relatively large light passage openings 15 according to the second embodiment according to FIGS. 4-6. The diameter of these light passage openings 16 is between 0.1 and 0.4 mm Such light passage openings are hardly able to be manufactured in the case of orthodontic appliances which are manufactured according to MIM technology or in a material-removing manner, and even if this were to be the case then this would practically be only with regard to the brackets and here too limited to the region of the slot. The preferred embodiment according to FIGS. 7-9 particularly advantageously permits a rapid and complete curing of a cement cured by light. In principle, it would be sufficient to merely provide the plane region 2' of the base plate 2 with light passage openings 16, in the case of these versions.

The invention moreover provides means which protects the orthodontic apparatus 1 on applying a cement onto the side 18 of the base plate 2 which comes to lie towards the tooth, so that cement can only get to where it should, said means moreover serving for applying the apparatus 1 onto the tooth. This means is hereinafter called applicator or protector and is indicated in the Figures at 20. The applicator 20 comprises a holding plate 21 which in the assembled condition lies with one end on the plane region 2' of the base plate 2 and extends upwards perpendicularly on this base plate 2. An integrally formed bead 22 is evident on the holding plate 22, at the gingival side. This integrally formed bead 22 fills the complete inner region of the gingival rolling-in 8. The applicator 20 thus covers all possibly present light passage openings 15 and 16, with the exception of those light passage openings which lie within the region of the occlusal rolling-in 7. A separate part which is represented as a sealing rod 23 can be present for this. One can of course make do without this sealing rod 23 if no light passage openings 15 or 16 are present within the region of the occlusal rolling-in 7. As the name already suggests, the applicator 20 in particular serves for applying the orthodontic appliance 1 onto a tooth. The holding plate 21 with the integrally formed bead 22 can be inserted into the orthodontic appliance from the side. The applicator 20 is then held with a positive and non-positive fit in the inserted condition. The non-positive or friction fit results due to the occlusal rolling-in 7 pressing laterally onto the holding plate 21, whereas the holding bead 22 forms the positive fit in the gingival rolling-in.

Figure 14:
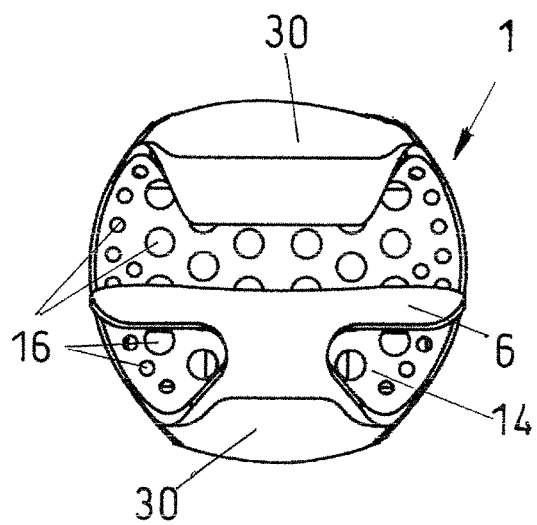
FIGS. 13-15 again show the orthodontic appliance, after removal of the applicator, with the deposited bonding layer and finally
Figure 13:
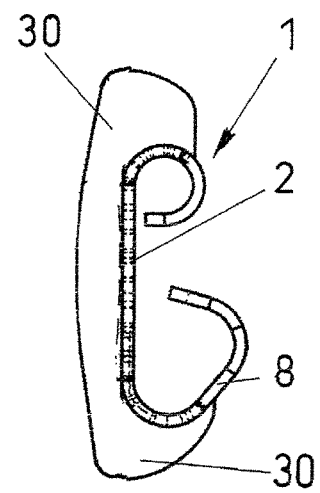
Figure 15:
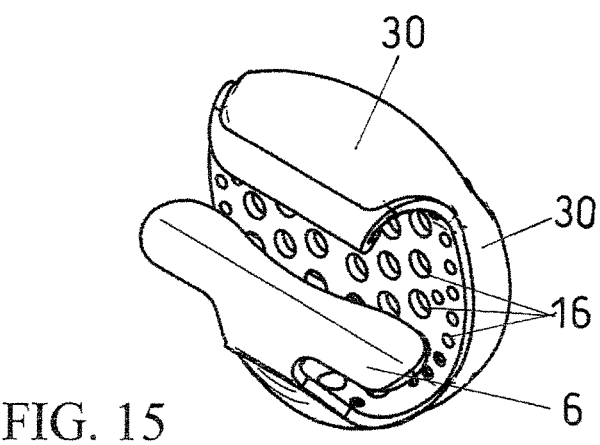

The orthodontic appliance according to FIGS. 7-9 is now represented with it being provided with cement 30, in the FIGS. 13-15. All other embodiments can be provided with cement in just the same manner, although this has not been shown. The applicator or protector 20 is removed here. The gingival rolling-in 8 here corresponds to the embodiment as with the version according to FIGS. 1-3. FIGS. 16-18 finally show the orthodontic appliance 1 according to the embodiment in FIGS. 4-6. Here, the possibility of such an appliance 1 being able to be additionally provided with an insert part 40 is additionally represented. This insert part 40 above all serve for fasting pull chains which serve for slinging or looping onto impacted teeth. With an orthodontic appliance according to FIGS. 4-6 as represented here, or with that according to FIGS. 7-9, one can also attach such appliances onto teeth which have hardly broken through due to an intense narrowing or restriction. In the usual case, a large enamel surface needs to be exposed, so as to be able to attach the appliance and so that enough light gets to below the appliance. This entails the danger of an accidental injury of the periodontium. An injury to the periodontium leads to ankylosis and to the loss of the tooth. However, it often merely leads to the orthodontic appliance dropping off and another operative intervention being required. The appliance according to the invention is significantly smaller compared to those which are obtainable on the market today. It has a base surface of only maximally 2 mm×2.5 mm and a construction height projecting from the tooth of 1.0 mm or less. This is therefore the smallest tube having a hook, compared to the solutions which are present on the market today.

The insert part 40 comprises a clamping plate 41 which engages in the rolling-ins 7 and 8 on both sides. The eyelet plate 42 is integrally formed perpendicularly and centrally on the clamping plate 41. This eyelet plate 42 comprises an eyelet, on which pull means, in particular pull chains can be hung. The clamping plate 41 at its ends comprises the contact arches 44 which engage into the rolling-ins 7 and 8 and which are adapted to the radii of these rolling-ins.

FIGS. 19-21 show an orthodontic appliance 1 with an elongate bead 19 which is embossed in the base plate by way of a stamping tool. This bead runs parallel to the gingival and to the occlusal edge 3, 4. An additional space for receiving cement arises on the bonding side 18 of the base plate 2 on account of this.

A spring-elastic shape retention of the occlusal rolling-in 7 can be avoided according to the solution in FIGS. 22-25. Here, a U-shaped stamp-out 19' is provided in the base plate 2 of the orthodontic appliance 1. A spring tongue 19" then remains within this U-shaped stamp-out 19'. The tongue 19" is bent upward slightly out of the base plate 2 during the stamping-bending procedure, so that this tongue bears on the free end of the occlusal rolling-in 7 forming the tube 5.

Apart from the already described significant advantages with regard to the use of the orthodontic appliance according to the invention, it is also not insignificant to the user that the solution according to the invention can be manufactured much more inexpensively than those solutions which have hitherto been available on the market, whose manufacturing methods are significantly more costly than the stamping-bending method of the solution according to the invention.

LIST OF REFERENCE NUMERALS 1 orthodontic apparatus
2 base plate
B archwire
2' plane region of 2
3 gingival edge
4 occlusal edge
5 lube 6 hook, wing-like
7 occlusal rolling-in
8 gingival rolling-in
9 side edges
10 first bend of the gingival rolling-in
11 straight section of the gingival rolling-in
12 second bend of the gingival rolling-in
13 straight end section of the occlusal rolling-in
14 concave indentations
15 light passage openings, large
16 light passage openings, small
17 single bend
18 bonding side
19 elongate bead
19' U-shaped stamp-out
19" spring tongue
20 applicator, protector
21 holding plate
22 integrally formed bead
23 sealing rod in 7
30 cement
40 insert pan
41 clamping plate
42 eyelet plate
43 eyelet
44 contact arches, flush with 15

The invention claimed is:

1. An orthodontic appliance comprising a weld-free and solder-free base plate having side edges and a planar region having a bonding region configured to be directed to a tooth, a gingival edge and an occlusal edge, wherein the occlusal edge is rolled away from the bonding region of the base plate by at least 200° to form a circular occlusal tube configured for receiving an archwire and the gingival edge is rolled away from the bonding region of the base plate by at least 150° to form a rolled gingival region having two opposite sides, and wherein the rolled gingival region comprises indentations in each of the two opposite sides forming hooks near the gingival edge configured for connecting orthodontic accessories.

2. The orthodontic appliance according to claim 1, wherein light passage openings are formed at least in the planar region of the base plate.

3. The orthodontic appliance according to claim 2, wherein the light passage openings comprise two openings which are arranged next to one another, whose combined areas correspond to between 30% and 60% of the planar region of the base plate.

4. The orthodontic appliance of claim 2 and an applicator/protector for placing the orthodontic appliance, wherein the applicator/protector has a holding plate comprising a planar section configured to be clamped gingivally and occlusally between the rolled gingival region and the occlusal tube, wherein the applicator/protector is configured to be inserted into the orthodontic appliance by way of an integrally formed bead provided on a gingival side of the holding plate, and wherein, when the applicator/protector is clamped to the orthodontic appliance, the applicator/protector completely seals off the light passage openings provided in the planar region of the base plate.

5. The applicator/protector according to claim 4, manufactured of transparent plastic.

6. The orthodontic appliance according to claim 1, wherein light passage openings are formed in the planar region of the base plate, along an axis of the base plate.

7. The orthodontic appliance according to claim 1, wherein an inner diameter of the occlusal tube corresponds approximately to the diameter of an archwire.

8. The orthodontic appliance according to claim 1, wherein the rolled gingival edge comprises two bends in the same rotation direction, with a flat section between the two bends.

9. The orthodontic appliance according to claim 8, wherein the indentations are formed in the flat section between the two bends.

10. The orthodontic appliance according to claim 1, additionally comprising an insert part having a clamping plate that engages the occlusal tube and rolled gingival region and an extending eyelet plate having an eyelet.

11. The orthodontic appliance according to claim 1, comprising an elongate bead embossed in the base plate parallel to the occlusal edge, extending away from the bonding region.

12. The orthodontic appliance according to claim 1, comprising a U-shaped stamp-out defining a spring tongue formed in the base plate, said spring tongue having a free end pointing to the occlusal tube and bearing on the occlusal tube.

13. The orthodontic appliance of claim 1 and an applicator/protector for placing the orthodontic appliance, wherein the applicator/protector has a holding plate comprising a planar section configured to be clamped gingivally and occlusally between the rolled gingival region and the occlusal tube, and wherein the applicator/protector is configured to be inserted into the orthodontic appliance by way of an integrally formed bead provided on a gingival side of the holding plate.

14. The applicator/protector according to claim 13, manufactured of transparent plastic.

* * * * *